Figure 1:
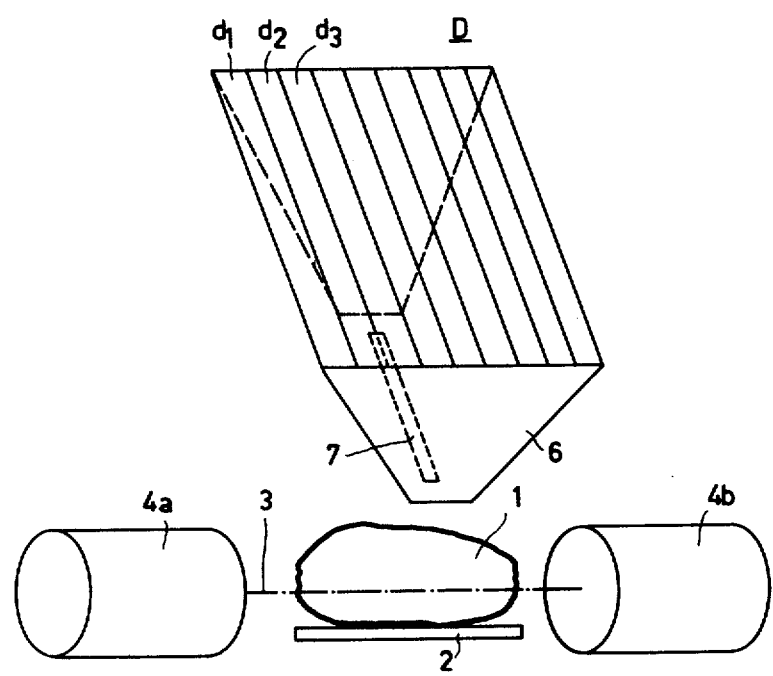

United States Patent [19]

Harding et al.

[11] 4,380,817

[45] Apr. 19, 1983

[54] METHOD FOR EXAMINING A BODY WITH PENETRATING RADIATION

[75] Inventors: Geoffrey Harding, Rellingen; Wolfgang Wagner, Hamburg, both of Fed. Rep. of Germany

[73] Assignee: U.S. Philips Corporation, New York, N.Y.

[21] Appl. No.: 185,845

[22] Filed: Sep. 10, 1980

[30] Foreign Application Priority Data

Sep. 27, 1979 [DE] Fed. Rep. of Germany ....... 2939146

[51] Int. Cl.³ ............................................. G01N 23/20
[52] U.S. Cl. ............................................. 378/87; 378/6
[58] Field of Search ........... 250/272, 273, 274, 277 R, 250/278, 279

[56] References Cited

U.S. PATENT DOCUMENTS

| | | | |
|---|---|---|---|
| 4,229,651 | 10/1980 | Danos | 250/272 |
| 4,258,256 | 3/1981 | Harding | 250/272 |
| 4,286,156 | 8/1981 | Wagner | 250/511 |

Primary Examiner—Craig E. Church
Attorney, Agent, or Firm—Jack E. Haken

[57] ABSTRACT

Devices that measure the electron density in a body by means of radiation scattered from a narrow pencil beam of penetrating radiation directed through the body, produce defective images on reconstruction of the density distribution because of multiple scattering of radiation. This can of course be reduced by scattered ray diaphragms, but cannot be eliminated entirely. The invention therefore provides a means for detecting the size of the multiple scattered radiation component be measurement. For this purpose, the detector array which measures radiation including the single scattered radiation, is screened, at least osscasionally, from the single scattered radiation and the detected intensity values measured by the detector elements when so screened, are used to correct the values generated by measuring the detected radiation including the single scattered radiation.

4 Claims, 7 Drawing Figures

METHOD FOR EXAMINING A BODY WITH PENETRATING RADIATION

The invention relates to a method of examining a body using penetrating radiation, in which a primary beam having a small diameter is directed through the body and scattered radiation thus generated is limited by a diaphragm arrangement and is measured by a detector array comprising a plurality of detector elements, after which the density distribution in the body along the primary beam is reconstructed from the measured values; it also relates to a device for implementation of the method. Such a method is known from DE-OS No. 27 13 581. The diaphragm arrangement in this case has a slit-shaped diaphragm aperture, which runs approximately at right angles to the direction of the primary beam. Through this slit-shaped diaphragm aperture there is a direct correspondence between a point on the primary beam and one of the detector elements of the detector array. In this way each detector element measures the scattered radiation from a different section along the path of the primary beam, which is a measure of the density of the body in that particular section.

Although scattered radiation is thus used to determine the density distribution, the measured results determined by the detector array are also falsified by scattered radiation. This is because part of the scattered radiation generated in the body along the primary beam, is scattered yet again, one or more times, and is generally incident through the slit-shaped diaphragm aperture, on a different detector from the scattered radiation which strikes the detector array directly from the source point of the repeatedly scattered radiation (hereafter referred to briefly as multiple scattered radiation, as opposed to the single scattered radiation generated directly by the primary beam).

It is already known that this multiple scattered radiation can be reduced by arranging, in front of the detector array, thin plates hereinafter referred to as lamellae, which are made of a highly radiation-absorbent material (e.g. lead), and which are positioned in planes that intersect colinearly approximately in and along the primary beam. In this way it is possible to eliminate to a large extent the scattered radiation travelling outside the above-mentioned plane but not the multiple scattered radiation travelling within the plane.

The aim of the present invention is thus to reduce further the effect of the multiple scattered radiation by measuring it and correcting the density distribution correspondingly.

Starting with a method of the kind mentioned in the introduction, this aim is achieved by screening at least some of the elements of the detector array, at least occasionally, from single scattered radiation and using the values measured by the detector elements when so screened, to correct values generated during a measurement including the single scattered radiation.

For this purpose it is assumed that the measured values originate from the additive superimposition of a component produced by the single scattered radiation and a further component produced by multiple scattered radiation, in which the local distribution of the intensities of the further component produced by multiple scattered radiation is subject to less fluctuation than that of intensities of the single scattered radiation. If at least some of the detector elements are now screened at least occasionally from the single scattered radiation, these detector elements will detect only the multiple scattered radiation and the values measured by these detector elements (the correction values) are then subtracted from the values obtained by measuring the combination of single scattered radiation and spurious multiple scattered radiation.

A device for the implementation of the method according to the invention, based on a device comprising at least one radiation source to produce the primary beam, a detector array to measure the scattered radiation generated in the body along the primary beam, a diaphragm arrangement placed between the detector array and the primary beam, having a slit-shaped aperture whose longitudinal direction is set at right angles to the primary beam; and a large plurality of lamellae made of radiation-absorbent material, arranged between the diaphragm aperture and the detector array, and which lie, at least approximately, in planes that intersect colinearly in and along the primary beam, is characterised by means for generating a relative displacement between the primary beam on the one hand, and the diaphragm arrangement, the detector array and the lamellae on the other hand, in such a way that the planes of the lamellae intersect outside the primary beam.

In a first arrangement this relative movement is achieved by a drive mechanism to shift the position of the detector array together with the diaphragm arrangement and the lamellae, in a direction longitudinally with respect to the slit-shaped diaphragm aperture. If, in this way, the detector array, together with the diaphragm and the lamellae, are moved far enough to the side, then only multiple scattered radiation can be measured by the detectors. The correction values thus detected must be multiplied by a factor which cancels out the change in the mean multiple scattered intensity caused by the aforesaid movement, before they are subtracted in order to correct the values of the direct measurements. This factor can be calculated once using measurements obtained from a phantom.

In a second arrangement, the relative movement between the primary beam, and the diaphragm arrangement, the detector array and the lamellae, is achieved by placing in front of the radiation source a stationary diaphragm with at least two apertures to form a plurality of spaced primary beams, and by placing, in front of this diaphragm a rotatable absorbing disc connected to a drive mechanism; this disc is provided with apertures which are arc-shaped with respect to the rotational axis. The apertures are arranged in staggered formation about the rotational axis and respectively at such a distance from the rotational axis that at any one time no more than one of the beams formed by the diaphragm can pass through an aperture in the absorber disc.

In this case the primary beam also changes its position with respect to the diaphragm arrangement.

Following a further development of this second arrangement, provision is made for the aperture in the absorber disc through which that primary beam passes which is directed along the line of intersection of the planes containing the lamellae, to have a longer length of arc than the other aperture or apertures. In this way the irradiation load on the patient during the detection of the multiple scattered radiation is reduced.

With the structure described so far, the radiation absorbing lamellae, whose planes intersect in the primary beam, were necessary. In a further arrangement in accordance with the invention, the lamellae can be dispensed with, which means that the construction of the detector array is simplified and its sensitivity increased. It is envisaged that, in a respective plane containing the diaphragm aperture and a corresponding scattering element of the body in the path of the primary beam, at any one time at least two detectors will be provided to generate corresponding individual signals, one of said detectors being screened from single scattered radiation by an absorber element. In this arrangement the measured values (generated by single and multiple scattered radiation) from the unscreened detector or detectors, and those from the detector element which is screened from the single scattered radiation, are therefore measured simultaneously.

Embodiments of the invention will now be described in more detail hereinafter by means of diagrams. These are as follows:

FIG. 1 A representation in perspective of a device in accordance with the invention.

Figure 2:
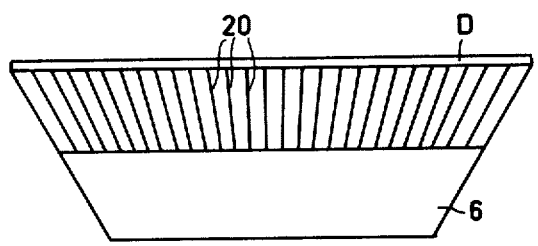
Figure 2:
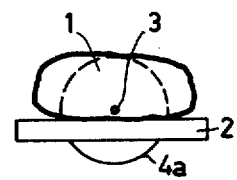

FIG. 2 A schematic representation of the device in a plane at right angles to the primary beam.

Figure 3:
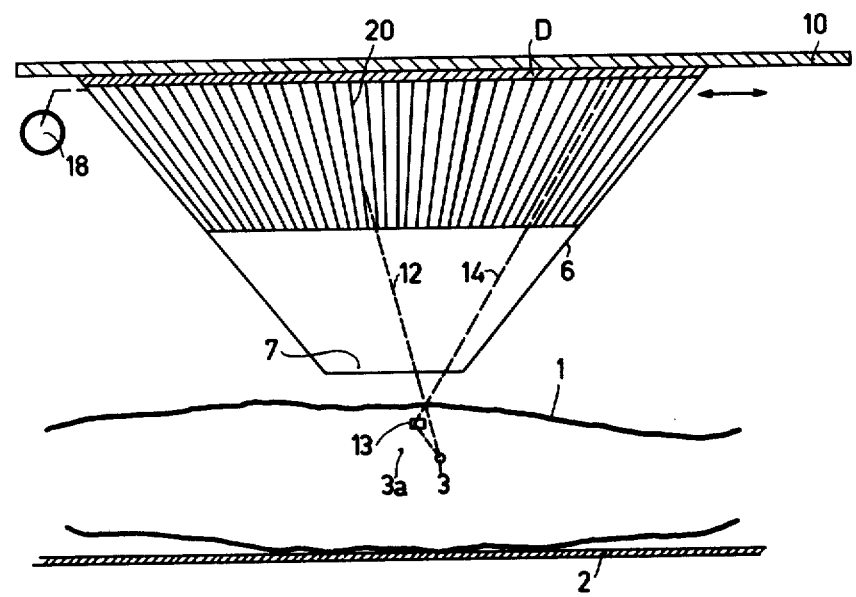

FIG. 3 The device after shifting the position of the diaphragm arrangement.

Figure 4:
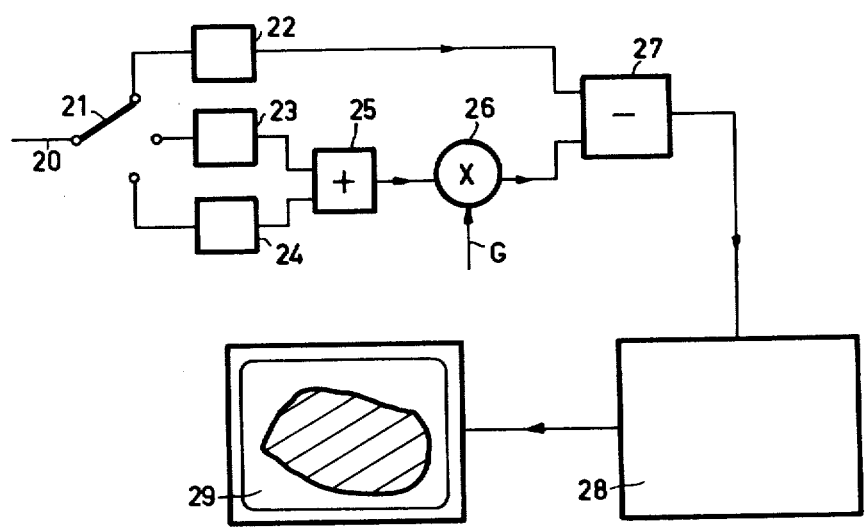

FIG. 4 A device for processing the signals arising from the method in accordance with the invention.

Figure 5:
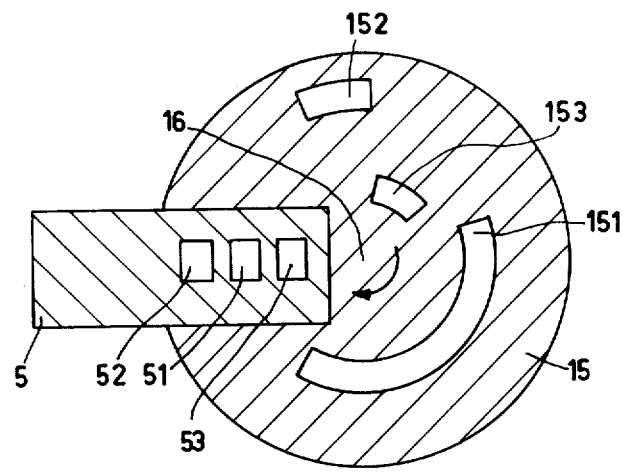

FIG. 5 A device for shifting the position of the primary beam with respect to the diaphragm, in a plane at right angles to the primary beam.

Figure 6:
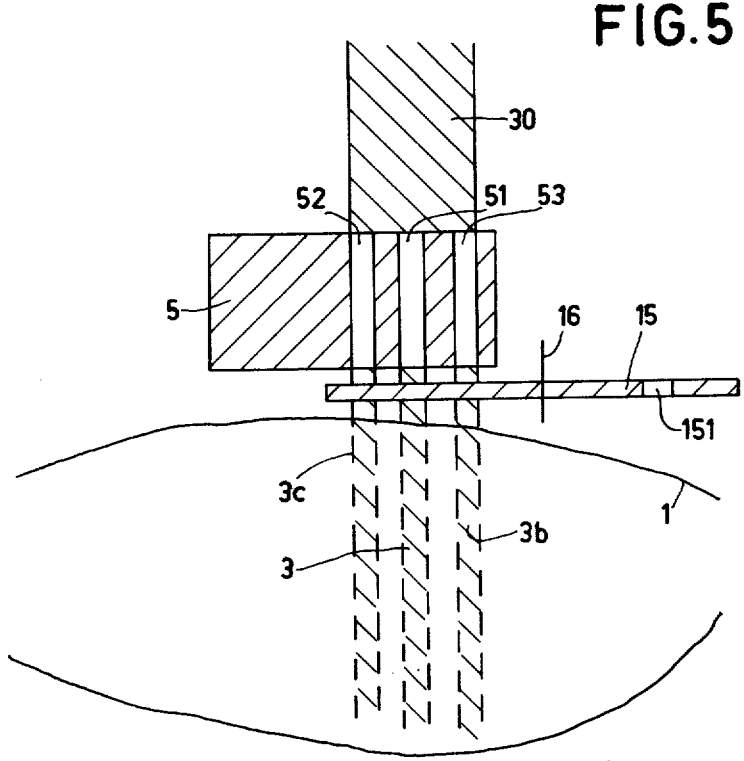

FIG. 6 The same device in a plane containing the primary beam, and

Figure 7:
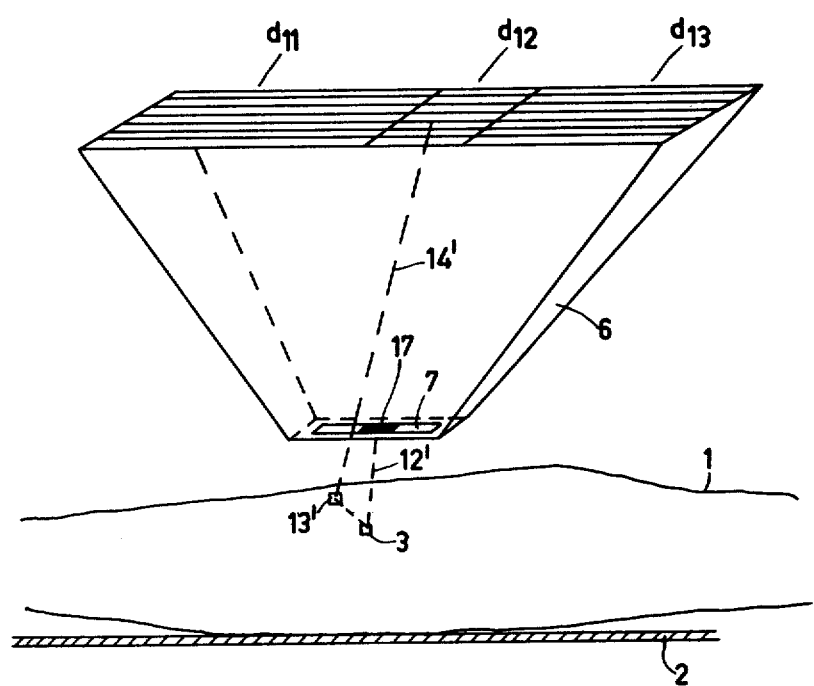

FIG. 7 A further arrangement for the implementation of the method.

In FIG. 1 the body to be examined 1 is represented lying on a tabletop 2. This body is irradiated by a primary beam 3 of penetrating radiation which is generated by X-ray tubes 4a, 4b positioned one on either side of the body, and limited by a diaphragm device (not shown). The dimensions of the limited primary beam determine the resolving power of the device. The smaller its cross-section, the better the resolving power.

The voltage applied to the X-ray tubes contained in the X-ray sources 4a and 4b is about 350 kV. On the one hand, the radiation density for the patient is therefore kept small and, on the other, the attenuation of the primary beam as a result of photo absorption is kept small as compared with attenuation as a result of Compton scatter.

The scattered radiation generated in the region of the body along the path of the primary beam 3, reaches a detector array D through a slit-shaped, preferably adjustable aperture 7 of a diaphragm arrangement 6 disposed above the body under examination. The detector array consists of a number of detector elements, $d_1$, $d_2$, $d_3$, etc., which are arranged adjacent to each other along a straight line parallel to the primary beam. As shown in FIG. 1, the surface of the detectors, which acts as a measuring surface, has the form of a rectangle, the longitudinal sides of which lie in a direction at right angles to the primary beam. The slit-shaped aperture 7 in the diaphragm arrangement 6 is of a corresponding shape; however, its dimensions in both directions are smaller than those of the detector in the ratio of its distance from the primary beam 3 to that of the detector elements. Through the slit-shaped aperture 7 in the diaphragm arrangement 6 there is a direct correspondence between a location along the path of the primary beam 3 and a detector element within the group of detectors D. The scattered radiation lobe generated by the primary beam at a certain point strikes the detector array D along a specific path which is assigned to one, or possible two, adjacent detector elements. In this way, every detector elements "sees" the scattered radiation emanating from a specific point or region in the path of the primary beam, with every point or region in the path of the primary beam corresponding to a different detector.

By shifting the relative position of the body 1 and the primary beam 3 directed through it, a different region of the body can then be irradiated and the density distribution therein can be detected by means of the detector array D. If this process is repeated for may different relative positions, the density distribution can be detected throughout any desired region of the body and this does not necessarily have to be a planar region.

An identically constructed arrangement of diaphragm and detectors can be placed under the tabletop 2. Each detector element is positioned to lie in a plane through the related diaphragm slit, which intersects the primary beam so as to detect the scattered radiation from the same region in the path of the primary beam as a corresponding detector in the first described array D; their respective output signals can thus be added.

FIG. 2 shows a cross-section of the primary beam 3 running at right angles to the plane of projection through the body 1 lying on the tabletop 2, and the diaphragm arrangement 6 and the detector array D arranged above the primary beam. The longitudinal direction of the individual detector elements and the slit run horizontally in this representation. Inside the diaphragm arrangement 6, a large number of lamellae 20 are arranged in front of the detector array. The lamellae lie in planes running at right angles to the plane of projection, and intersecting in the primary beam 3. Thus, the planes lie at right angles to the longitudinal direction of the individual detector elements and the longitudinal direction of the slit. As a result of this, the single scattered radiation will reach the detector array D practically unattenuated, while multiple scattered radiation will be absorbed by the metal lamellae 20 if it does not propagate in a plane containing the primary beam.

FIG. 3 shows that the diaphragm arrangement 6, together with the detector array and the lamellae 20, can be moved along a fixed rail 10 by means of a motor drive. The rail 10 runs parallel to the longitudinal direction of the slit-shaped aperture 7 and hence at right angles to the direction of the primary beam 3. In addition, the diaphragm arrangement is shown as having been moved sideways, so that the lamellae 20 no longer intersect in and along the primary beam 3, but in the axis 3a which is at right angles to the plane of projection; the distance between 3 and 3a indicates the shift compared with the position in FIG. 2. It will be seen that the single scattered radiation emanating from the primary beam 3—in the diagram, the beam 12 which is drawn in only by way of example—cannot reach the detector array D because it is absorbed by one of the lead lamellae 20. As against this multiple scattered radiation—in so far as it propagates in a suitable direction in the plane of a respective lamella—the beam 14 is drawn in as an example—can reach the detector array D via the passages between the lamellae. As the intensity of the multiple scattered radiation alters relatively little spatially, it can be assumed that the multiple scattered radiation measured in this position of the detector elements, will correspond approximately to the component due to multiple scattered radiation which the detector elements will measure (in addition to the single scattered radiation), when the lamellae are directed towards the primary beam 3 as in FIG. 2. It is useful as a third step to move the diaphragm arrangement in the other direction so that the planes of the lamellae intersect in an axis to the right of the primary beam 3 and to determine a correction value on the basis of the multiple scattered radiation found both in this position and in the position shown in FIG. 3.

FIG. 4 shows a device for processing the values obtained in this way. The measured values provided by a detector element of the detector array are applied—if necessary, after analog-to-digital conversion—via a lead 20 and a multiplexer 21, to one of three intermediate memories 22, 23 or 24. The multiplexer 21 is controlled by a control means (not shown in detail) in such a way that the first value measured in the position in which the planes of the lamellae intersect in the primary beam is stored in the memory 22, while the values measured in the other two lateral positions of the diaphragm arrangement are stored respectively in the intermediate memories 23 and 24. The values contained in the intermediate memories 23 and 24 are assumed by an adding device 25 and multiplied in a multiplying device 26 by a factor G. This factor is chosen so as to cancel the effect of overall sensitivity differences in detecting the intensities of the multiple scattered component detected together with the single scattered radiation (in the position shown in FIG. 2) on the one hand, and multiple scattered radiation detected on its own, (e.g. as a result of the intensity of the primary beam being reduced when multiple scattered radiation alone is detected), and, if necessary to compensate for the differences in the irradiation time of the detector elements in the different cases. The output signal of the multiplying device 26 is thus a measure of the intensity of the multiple scattered radiation in the first position (FIG. 2). The signal is subtracted in a subtracting device 27 from the signal stored in the intermediate memory 22, which is a measure of the total scattered radiation (single scattered radiation plus multiple scattered radiation). At the output of the subtracting device 27 a signal is therefore generated which essentially represents only the single scattered radiation measured by the relevant detector element and this signal is now fed to a computing and storage device 28.

Elements corresponding to the elements 20 and 27 can also be provided for the other detector elements. However it is also possible to add together the output signals of several adjacent detector elements in those positions in which the lamellae intersect outside the primary beam, resulting in spatial integration of the multiple scattered radiation, and to subtract these values from the measured values representing the total scattered radiation (single plus multiple scattered radiation) measured in the position as in FIG. 2. Clearly, in this case, a different weighting factor must be chosen. Similarly, because of the fact that the multiple scattered radiation alters relatively little spatially, it is possible to use only some of the detector elements, e.g. every fourth detector element, to detect the multiple scattered radiation and to use the output signals of these elements to correct the values received from the adjacent detector elements. In the same way it is possible to utilise for all detector elements, only one adding device 25, one multiplying device 26 and one subtracting device 27, if the intermediate memories corresponding to the detector elements are connected to them in multiplex operation. In this case the subtraction circuit 27 will deliver the corrected values in sequence.

The reconstruction of the distribution of density in the computing and storage device 28 on the basis of the values corrected in this way, is relatively simple because in principle each value already represents the density at one specific point, as already explained in DE-OS No. 27 13 581. A display device 29, e.g. with a cathode ray tube, which displays the distribution of density visually, is connected to the computing and storage device 28.

The relative shift between the primary beam on the one hand and the diaphragm arrangement, together with the detector array and the lamellae on the other, required to detect the multiple scattered radiation, can alternatively be achieved, as mentioned above, by shifting the primary beam whilst keeping the diaphragm arrangement stationary. For this purpose the X-ray beam produced by the two X-ray sources 4a and 4b (FIG. 1) must be applied to the examination region by means of a device as shown in FIG. 5 and FIG. 6, in which respect FIG. 5 shows this device in a plane at right angles to the primary beam and FIG. 6 shows the device in the same plane as the primary beam.

The primary radiation beam 30, which initially is of relatively large cross-section (FIG. 6), is directed onto a stationary collimator diaphragm 5, which has three parallel passages 51, 52 and 53 next to each other in a straight line. The primary beam 30 is split up by these passages into three primary beams 3, 3c and 3b (FIG. 6). The three primary beams thus generated, are incident on a circular absorber disc 15, driven by a motor (not further illustrated), and which rotates about an axis 16 directed parallel to the primary beam and situated approximately in the same plane as their central axes. The absorber disc 15 has three arcuate apertures 151, 152, and 153, in staggered arrangement about the rotation axis, and located respectively at various distances from said axis in such a way that when the absorber disc 15 rotates in a clockwise direction, first the aperture 151 is presented in front of the passage 51 and allows the primary beam 3 to pass through, then the aperture 153 is presented in front of the passage 53 allowing the primary beam 3b to pass through, and finally the recess 152 is presented in front of the passage 52 allowing the primary beam 3c to pass through. Assuming that the diaphragm, lamellae and detector arrangement, corresponding to that shown in FIG. 3, is stationary and arranged in such a way that the planes intersect in the primary beam 3, then (as long as the aperture 151 is present in front of the passage 51) the total scattered radiation (single+multiple scattered radiation) is measured first by the detector and then—as long as one of the two apertures 153 and 152 is present in front of a corresponding one of the two passages 53 and 52 respectively—the multiple scattered radiation alone is measured. If (as shown in FIG. 1) two X-ray sources are used, care must be taken to ensure that the absorber disc run synchronously on both sides of the examination region so that corresponding primary beam paths are followed in succession.

As can be seen in FIG. 5, the aperture 151 has a considerably longer length of arc than the apertures 152 and 153—so that—given a constant rotational speed—the primary beam 3 irradiates object 1 for longer than the primary beams 3c and 3b, in proportion to the relationship between the arc of length of the aperture 151 and those of the other two apertures. Because of this more photons can be detected when determining the total scattered radiation, and this increases the accuracy of measurement.

FIG. 7 represents an arrangement, in which the use of lamellae to screen off a large proportion of the multiple scattered radiation is not required. The diaphragm arrangement 6 is constructed in exactly the same way as the arrangement in FIG. 1, i.e. it has a slit-shaped aperture 7 whose longitudinal direction is set at right angles to the primary ray 3. Here also, the detector array consists of separate strip-shaped elements; however, these are divided in the longitudinal direction, into three parts (the elements $D_1$, in FIG. 1 for example is divided into the three parts $d_{11}$, $d_{12}$ and $d_{13}$) whose output signals are processed independently of each other. In the slit-shaped aperture 7 is located an absorber element 17 which screens off one section, preferably the centre section ($d_{12}$ and the corresponding elements of the other detector strips), against single scattered radiation generated in the primary beam, whilst the single scattered radiation generated in the primary beam can strike directly both the other sections ($d_{11}$, $d_{13}$ and the corresponding elements of the other detector strips). Thus, both the latter sections measure the total scattered radiation (single + multiple scattered radiation), whereas the central section only measures the multiple scattered radiation, which is generated, for example, at a point 13', and corresponds to ray 14', and strikes the central section of the detector array ($d_{12}$, etc.) through the slit 7 by-passing the absorber element 17.

The values obtained from the elements $d_{11}$ and $d_{13}$ can be added together, after which the value obtained from the central detector element $d_{12}$—with a suitable weighting corresponding to the effective size of the detector surfaces—is subtracted from the resulting total value.

The structure as shown in FIG. 7, in comparison with the structures hereinbefore described, has the advantage that no mechanical movement is necessary, but a greater number of detector elements is required.

So far the invention has been described in connection with devices which are already known from German patent applications Nos. 27 13 581 and 27 57 320. However, the invention can also be used with other devices, e.g. in accordance with German patent application No. 26 55 230.

What is claimed is:

1. In a device for examining a body using penetrating radiation which comprises: source means which generate a primary beam of said radiation, detector array means for measuring, and for generating output signals representing, scattered radiation generated in the body along the primary beam, diaphragm means disposed between the detector array means and the primary beam which define a slit shaped aperture having a longitudinal direction which is oriented at right angles to the primary beam; and a large plurality of lamellae of radiation-absorbing material disposed between the aperture and the detector array means which lamellae are disposed at least approximately in planes which intersect colinearly in and along the primary beam whereby the detector array means measure radiation which is both singly and multiply scattered in the body; the improvement which comprises:

means for generating a relative displacement between the primary beam and the diaphragm means, the detector array means, and the lamellae so that, during a portion of the examination, the planes of the lamellae intersect outside of the primary beam whereby the detector array means only measure radiation which is multiply scattered in the body; and means which subtract output signals from the detectors which represent only said multiply scattered radiation from respective output signals which represent both singly and multiply scattered radiation to produce signals which represent only singly scattered radiation.

2. A device as claimed in claim 1 further comprising drive means which function to shift the detector array means, the diaphragm means, and the lamellae in a longitudinal direction with respect to the aperture.

3. A device as claimed in claim 1 further comprising:

a stationary diaphragm, disposed between the radiation source means and the body, which defines at least two apertures which function to form a plurality of spaced primary beams;

rotatable absorber disc means, disposed between the stationary diaphragm and the body, which defines a plurality of arc-shaped apertures which are concentric with a rotational axis of the disc and are arranged in staggered formation about said rotational axis so that no more than one of the primary beams can pass through the disc means at any time; and means for rotating the disc means about the axis.

4. A device as claimed in claim 3 wherein a first of the arc-shaped apertures is positioned to pass a primary beam in which the planes the lamellae intersect and wherein the length of arc of said first aperture is greater than the length of arc of the other apertures defined by the disc means.

* * * * *